(12) United States Patent
Ono et al.

(10) Patent No.: US 7,182,972 B2
(45) Date of Patent: *Feb. 27, 2007

(54) WATER-SOLUBLE BEAN-BASED EXTRACTS

(75) Inventors: Mitsunori Ono, Lexington, MA (US);
Keizo Koya, Chestnut Hill, MA (US);
Noriaki Tatsuta, Lexington, MA (US);
Naoto Yamaguchi, Ibaraki (JP); Lan Bo Chen, Lexington, MA (US)

(73) Assignee: Quercegen Pharma, LLC, Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/747,021

(22) Filed: Dec. 23, 2003

(65) Prior Publication Data

US 2004/0175475 A1    Sep. 9, 2004

Related U.S. Application Data

(60) Continuation of application No. 10/440,344, filed on May 15, 2003, now abandoned, which is a continuation of application No. 10/006,326, filed on Nov. 13, 2001, now Pat. No. 6,616,959, which is a division of application No. 09/489,059, filed on Jan. 21, 2000, now Pat. No. 6,458,406.

(60) Provisional application No. 60/240,906, filed on Dec. 17, 1999.

(51) Int. Cl.
*A23L 1/20* (2006.01)
*A23L 1/40* (2006.01)
*A23L 1/48* (2006.01)
*A23L 2/00* (2006.01)
*A23F 5/00* (2006.01)
*A23F 3/00* (2006.01)
*A23G 3/00* (2006.01)

(52) U.S. Cl. ............... 426/634; 426/629; 426/655; 426/539; 426/594; 426/599; 426/590; 426/631

(58) Field of Classification Search ............ 426/634, 426/629, 655, 539, 594, 599, 590, 3, 631
See application file for complete search history.

(56) References Cited

U.S. PATENT DOCUMENTS 2,881,076 A    4/1959    Sair (Continued)

FOREIGN PATENT DOCUMENTS

EP    0 906 761 A2    4/1999

(Continued)

OTHER PUBLICATIONS

Fukutake et al., "Quantification of Genistein and Genistin in Soybeans and Soybean Products," 1996, 34:457-461.

(Continued)

*Primary Examiner*—Anthony Weier
(74) *Attorney, Agent, or Firm*—Fish & Richardson P.C.

(57) ABSTRACT

This invention relates to a water-soluble bean-based extract including one or more isoflavone glycosides. Also INCLUDED is a method of preparing such a water-soluble bean-based extract.

12 Claims, 1 Drawing Sheet

U.S. PATENT DOCUMENTS

| | | | | |
|---|---|---|---|---|
| 4,119,733 | A | | 10/1978 | Hsieh et al. .................. 426/46 |
| 4,776,104 | A | | 10/1988 | Kuoyama ...................... 34/77 |
| 4,892,746 | A | | 1/1990 | Donida et al. ............. 426/598 |
| 5,043,326 | A | | 8/1991 | Stadler née Szoke et al. 514/58 |
| 5,141,746 | A | | 8/1992 | Fleury et al. ............... 424/757 |
| 5,170,697 | A | | 12/1992 | Kuboyama .................. 99/470 |
| 5,206,050 | A | | 4/1993 | Jennings ..................... 426/656 |
| 5,558,006 | A | | 9/1996 | Kuboyama .................. 99/275 |
| 5,572,923 | A | | 11/1996 | Kuboyama .................. 99/287 |
| 5,637,561 | A | | 6/1997 | Shen et al. ..................... 514/2 |
| 5,670,632 | A | | 9/1997 | Chaihorsky .................... 536/8 |
| 5,710,270 | A | | 1/1998 | Maeda et al. ................ 536/124 |
| 5,789,581 | A | * | 8/1998 | Matsuura et al. ........... 536/128 |
| 5,847,108 | A | | 12/1998 | Kanaoka et al. ............ 536/103 |
| 5,882,717 | A | | 3/1999 | Panesar et al. ............. 426/595 |
| 5,994,508 | A | * | 11/1999 | Bryan et al. ................ 530/378 |
| 6,004,558 | A | | 12/1999 | Thurn et al. ............. 424/195.1 |
| 6,015,785 | A | | 1/2000 | Shen et al. ..................... 514/2 |
| 6,020,471 | A | | 2/2000 | Johns et al. .................... 536/8 |
| 6,033,714 | A | | 3/2000 | Gugger et al. ............. 426/634 |
| 6,083,553 | A | | 7/2000 | Waggle et al. ............. 426/629 |
| 6,458,406 | B1 | * | 10/2002 | Ono et al. .................. 426/634 |

FOREIGN PATENT DOCUMENTS

WO      WO 99/38509      8/1999

OTHER PUBLICATIONS

Kim et al., "Intestinal Bacterial Metabolism of Flavonoids and Its Relation to Some Biological Activities," Arch. Pharm. Res., 1998, 21:17-23.

Messina et al., "Soyfoods and Cancer Prevention," The Simple Soybean and Your Health, 1994, 8:77-86.

Messina et al., "Four More Western Ailments," The Simple Soybean and Your Health, 1994, 11:113-121.

Wang et al., "Isoflavone Content in Commercial Soybean Foods," J. Agric. Food Chem., 1994, 42:1666-1673.

Xie et al., "Daidzin, an Antioxidant Isoflavonoid, Decreases Blood Alcohol Levels and Shortens Sleep Time Induced by Ethanol Intoxication," Alcoholism: Clinical and Experimental Research, 1994, 18:1443-1447.

Yasuda et al., "Urinary and Biliary Metabolites of Daidzin and Daidzein in Rats," Biol. Pharm. Bull., 1994, 17:1369-1374.

Yasuda et al., "Urinary Metabolites of Daidzin Orally Administered in Rats," Biol. Pharm. Bull., 1998, 21:953-957.

* cited by examiner

WATER-SOLUBLE BEAN-BASED EXTRACTS

CROSS REFERENCE TO RELATED APPLICATIONS

This application is a continuation of U.S. Utility Application 10/440,344, filed on May 15, 2003 now abandoned, which is a continuation of U.S. Utility Application 10/006,326, filed on Nov. 13, 2001, now U.S. Pat. No. 6,616,959, which is a divisional of U.S. Utility Application 09/489,059, filed on Jan. 21, 2000, now U.S. Pat. No. 6,458,406, which claims priority to U.S. Provisional Application 60/240,906, filed on Dec. 17, 1999, now abandoned, which was converted to a Provisional from U.S. Utility Application 09/464,260.

BACKGROUND

One of the newest and most intriguing areas of nutrition investigation involves food components called phytochemicals. Phytochemicals, such as isoflavones and their derivatives, are found only in plants, and although they are not classified as nutrients, they profoundly affect our health. See, for example, "Phytochemicals, A new paradigm" edited by W. R. Bidlack et al., published by Technomic publishing Co., Inc, 1998.

The discovery of phytochemicals has caused the dawning of a new era in nutrition. The phytochemicals found in beans, such as soybeans, are of particular interest. Beans and the products made from them, e.g., soybeans and soybean products, offer a unique approach to lowering the incidence of many chronic diseases such as cancer. See, for example, Journal of Agricultural Food Chemistry, 42, 1666 (1994); i.d., 43, 1184 (1995). Recently, research shows that consuming just one serving of soy foods a day may be enough to obtain the benefits of these phytochemicals. (See "The simple soybean and your health" by M. Messina et al., published by Avery publishing Group, Garden City Park, N.Y., 1994).

Many people, however, do not like to eat soy foods because of their smell, taste, and texture. One way to obviate the dislike of soy foods would be to take soybean isoflavones as dietary supplements. Unfortunately, soybean isoflavones and their derivatives have not been utilized as dietary supplements because of their low solubility in water. See "Genistein" by R. Elkins, published by Woodland Publishing, Pleasant Grove, Utah 1998.

SUMMARY

In one aspect, the invention features a water-soluble bean-based dry or wet extract including one or more isoflavone derivatives of the formula:

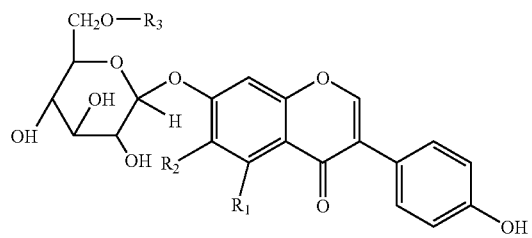

where $R_1$ is hydrogen or hydroxy, $R_2$ is hydrogen or methoxy, $R_3$ is hydrogen or CO—$R_4$, $R_4$ being methyl or carboxymethyl. The water-soluble bean-based extract, in dried form, includes from about 5 to about 50 parts by weight of isoflavone derivatives and has a solubility from about 10 mg/ml to about 1,000 mg/ml in water at about 25° C. Examples of isoflavone derivatives present in the water-soluble bean-based extract include daidzin, genistin, glycitin, 6"-O-acetyldaidzin, 6"-O-acetylgenistin, 6"-O-acetylglycitin, 6"-O-malonyldaidzin, 6"-O-malonylgenistin, or 6"-O-malonylglycitin.

The water-soluble bean-based extract of this invention includes one or more isoflavone derivatives, e.g., an isoflavone glycoside, which complex with other components contained in beans to unexpectedly enhance their solubility in water.

In another aspect the invention features a method of preparing a water-soluble bean-based extract. The method includes mixing pulverized crude bean extract with water, heating the mixture, adding a coagulant to the mixture to form a suspension, heating the suspension, and collecting the supernatant to obtain a water-soluble bean-based extract.

The water-soluble bean-based extract of this invention has a pleasant taste and smell, and exhibits desirable composition and performance when used as an ingredient in any food product. For example, the water-soluble bean-based extract can be combined with a food product such as milk, tea, soft drink, juice, coffee, seasoning, cereal, water, beer, cookies, chewing gum, chocolate, or soup.

Other features and advantages of the invention will be apparent from the following detailed description, and from the claims.

DETAILED DESCRIPTION

Figure 1:
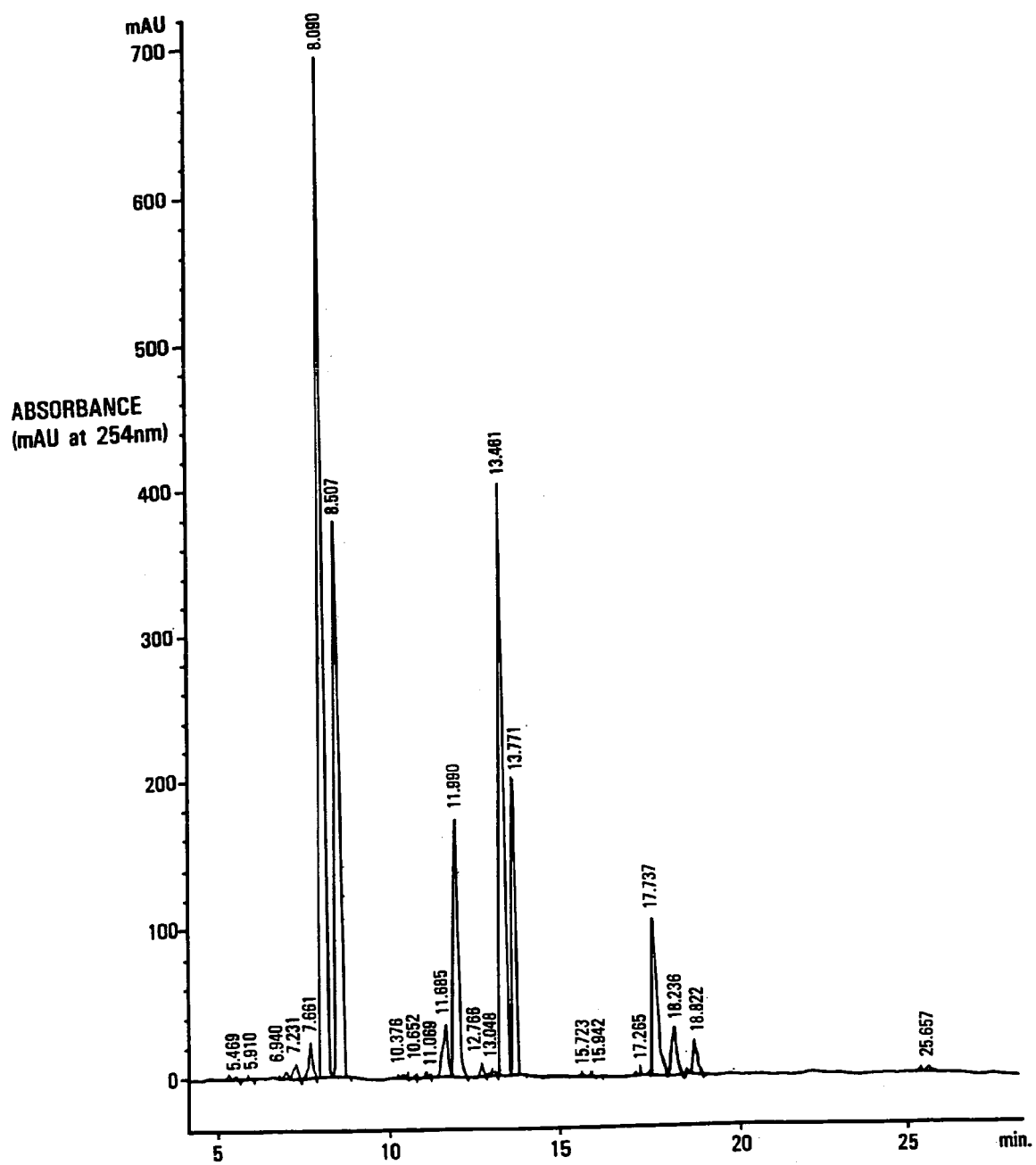
FIG. 1 shows the HPLC chart of the major components in the water-soluble bean-based extract prepared in Example 1.

The present invention relates to a water-soluble bean-based extract including isoflavone derivatives having the formula:

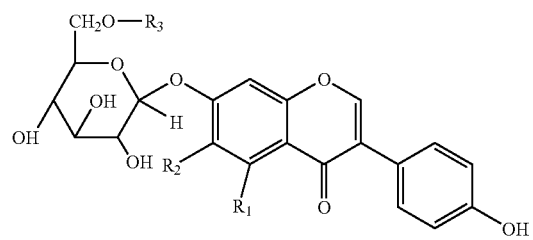

wherein $R_1$ is hydrogen or hydroxy, $R_2$ is hydrogen or methoxy, $R_3$ is hydrogen or CO—$R_4$, $R_4$ being methyl or carboxymethyl.

Examples of isoflavone derivatives present in an extract of this invention are daidzin, genistin, glycitin, 6"-O-acetyldaidzin, 6"-O-acetylgenistin, 6"-O-acetylglycitin, 6"-O-malonyldaidzin, 6"-O-malonylgenistin, and 6"-O-malonylglycitin. Isoflavone glycosides, such as daidzin and genistin, are absorbed in the stomach or small intestine and metabolized to isoflavones via aglycones by human intestinal microflora producing rhamnosidase, exo-beta-glucosidase, endo-beta-glucosidase or beta-glucuronidase. See, for example, Biol.

Pharm. Bull., 21 (1998); Biol. Pharm. Bull., 17, 1369 (1994); and Arch. Pharm. Res., 21, 17 (1998).

The water-soluble bean-based extract of this invention has increased water solubility which improves the physiological absorption of the isoflavone derivatives into the body when used in food products. For instance, the solubility of genistin is about 5 mg/ml in methanol and about 1 mg/ml in water at 25° C., whereas the solubility of the water-soluble bean-based extract of this invention, containing at about 10 percent of isoflavone derivatives, is about 300 mg/ml in water. Typically, the water-soluble bean-based extract of the invention provides an increase of about 30 fold in the solubility of isoflavone derivatives. In dried form, it includes from about 5 to about 50 parts by weight of isoflavone derivatives and has a solubility from about 10 mg/ml to about 1,000 mg/ml in water at about 25° C.; preferably, about 10 to about 20 parts by weight of isoflavone derivative and having a solubility from about 30 mg/ml to about 300 mg/ml; and more preferably, about 10 to about 20 parts by weight of isoflavone derivatives and having a solubility from about 50 mg/ml to about 200 mg/ml. Of course, the weight percentage of isoflavone derivatives affects the overall solubility of the water-soluble bean-based extract. For instance, the overall solubility of an extract having a higher weight percentage of isoflavone derivatives will be less than an extract containing a lower weight percentage of isoflavone derivatives.

Any variety of beans can be used to make the water-soluble bean-based extract of this invention. Examples of beans used in making the water-soluble bean-based extracts include but are not limited to soybeans, mung beans, black beans, and kidney beans. Preferably the beans are soybeans. In general, there are two different types of soybeans, e.g., food beans and oil beans, which can be used to make the water-soluble bean-based extract of this invention. Oil beans are preferred since they have smaller amounts of proteins relative to food soybeans. Typically, oil soybeans are first processed to produce "processed" soybeans by eliminating soybean oil. Examples of processes for eliminating soybean oil can be found in "Soybean Chemistry, Technology, and Utilization", by K. S. Liu, Aspen Publishers, Inc. Gaithersburg, Md. 1999.

A method of preparing the water-soluble bean-based extract of this invention includes mixing about 1 to about 50 parts by weight of a pulverized crude bean extract with about 100 parts by weight of water (hot or cold). An example of a bean crude extract is soy germ. A crude bean extract can be obtained by solid-liquid extraction. For example, crushed beans can be extracted with about 50% to about 90% aqueous alcohol or 100% organic solvents, such as ethanol, methanol, or acetonitrile. A crude bean extract can also be obtained by solid-solid extraction, e.g., gravity based separation. For example, soy germ can be separated from soybeans by solid-solid extraction based on its density difference from the remaining soybean portions. Soy germ represents about 1% by weight of soybeans yet contains a higher concentration of isoflavone derivatives relative to the remaining soybean portions. For example, the concentration of isoflavone derivatives in soy germ is about 6 times greater than the remaining soybean portions. See, for example, "Soybean Chemistry, Technology, and Utilization", by K.S. Liu, Aspen Publishers, Inc. Gaithersburg, Md. 1999. A pulverized crude bean extract, such as soy germ, can be obtained from Schouten USA, Inc.

The mixture of water and pulverized crude bean extract is then heated to between about 60° C. and about 100° C. for about 10 to about 120 minutes and between about 0.001 to about 3.0 parts by weight of coagulant per about 100 parts by weight of water is added to the mixture to form a suspension, which is heated again to between about 30° C. and about 100° C. for about 1 to about 120 minutes. The supernatant is subsequently collected, e.g., by filtration or centrifugation, to obtain a water-soluble bean-based extract having increased solubility. Additionally, the pH of the suspension or supernatant can be adjusted by adding acids or bases to avoid precipitating isoflavone derivatives. Typically, the pH is adjusted to about 6.0. After removing the supernatant, the residue can be extracted repeatedly to maximize the yield of the water-soluble bean-based extract.

The supernatant thus obtained can be decolorized to remove any undesirable color. Decolorizing methods include, but are not limited to, hydrogenation with the aid of a nickel catalyst, and other bleaching techniques used in the manufacture of soybean oils. Decolorizing methods can be found, for example, in "Soybeans, Chemistry, Technology, and Utilization" by K. Liu, published by An Aspen Publication, 1999, and "In Introduction to oils and fats Technology" edited by P. J. Wan, p-95, published by AOCS Press, Champaign, Ill. The supernatant can also be concentrated by any distillation system known in the art, including but not limited to molecular distillation or evaporation. An example of a molecular distillation system is a Wiped-Film Still, available from POPE SCIENTIFIC, INC, located at 351 N. Dekora Woods Blvd. Saukville, Wis. 53080, USA. Additionally, the supernatant can be dried by any drying method known in the art, such as lyophilization or spray-drying. (See, for example, U.S. Pat. No. 5,882,717).

The water-soluble bean-based extract of this invention can be produced by a batch method or a flow method, i.e., a continuous extraction and filtration process. Typically, flow processes are used to help maintain reasonable manufacturing costs.

The solubility of isoflavone glycosides is enhanced by the addition of about 0.001 to 3.0 parts by weight of a coagulant, such as $CaCl_2$, $CaSO_4$, $MgCl_2$, $MgSO_4$, any organic or inorganic acid, (e.g., citric acid, fumaric acid, lactic acid, malic acid, tartaric acid, $H_2SO_4$, $H_3PO_4$, or HCl), saccharin, glucono-D-lactone, and papain in 100 parts by weight of water. When preparing the extract, adding the coagulant tends to form insoluble aggregates of bean proteins or polysaccharides by simple cross-linking or denaturing. The concentration of coagulant directly affects the amount of proteins or polysaccharides in the extract. For example, larger amounts of coagulant cause more insoluble aggregates to form. This effect permits control of the total amount of water-soluble proteins and polysaccharide in the extract, as well as the solubility of the isoflavone derivatives. The amount of coagulant to be added can be determined by measuring the fat, protein, and inorganic salt content of the resultant bean-based extract. In general, enough coagulant is added to produce an extract having less than about 1% of fat, between about 1% to about 5% of protein, between about 0.01% to about 3% of Na, between about 0.01% to about 3% of Ca, and between about 0.01% to about 3% of any acids. The amount of fat, protein, Na, Ca, and acid in the water-soluble bean-based extract can be determined by any known analytical method, such as by following the analytical methods recommended by the Food and Drug Administration (FDA). Typically, about 0.3 parts by weight of citric acid is added to the extract. In general, if too much coagulant is added, the water-soluble bean proteins, polysaccharides, or isoflavone derivatives co-precipitate out of the extract thereby decreasing the concentration of isoflavone derivatives in the extract or the solubility of the isoflavone derivatives. If too little coagulant is added, the bean-based mixture forms a colloid from which the water-soluble bean-based extract is not easily separated.

The water-soluble bean-based extract of this invention can be added to a food product either in dried or wet form. The food product can be a solid, a paste, or a liquid food product, such as milk, tea, soft drinks, juices, coffee, seasonings, cereals, water, beer, cookies, chewing gum, chocolate, or soups.

The water-soluble bean-based extract of this invention can also include co-extracts from other grains, such as barley, rice, and malts. For example, one or more other grains can be processed together with beans by the methodology described above to produce a water-soluble bean-based extract of this invention. Additionally the water-soluble bean-based extract can be fortified with electrolytes, flavors, preservatives, and other additives, (e.g., vitamin supplements and maltodextrin). Examples of preservatives include, but are not limited to, ascorbic acid and propyl gallate. Examples of electrolytes include, but are not limited to, magnesium sulfate and potassium chloride.

Without further elaboration, it is believed that the above description has adequately enabled the present invention. The following specific examples are, therefore, to be construed as merely illustrative, and not limitative of the remainder of the disclosure in any way whatsoever. All of the publications cited herein, including patents, are hereby incorporated by reference in their entirety.

EXAMPLE 1

Pulverized soybean crude product (1 kg) extracted with about 90% aqueous EtOH, i.e., SoyLife 150 purchased from Schouten USA, Inc., was added to 3 liters of hot water at 70° C. The mixture was stirred at 90° C. for 30 min and then at 50° C. for 30 min. The residue and solution were roughly separated by centrifuging the mixture at 10,000 ×g at 50° C. After decanting, 6 g of $CaCl_2$, food additive grade (about 0.02 M), was added to the supernatant and additional stirring was continued at 30° C. for 30 min. The supernatant was filtered through a 1-μm pore size microfilter and yielded a yellow solution (2.5 liters). The filtrate was then transferred into a 5-liter glass flask and was hydrogenated in the presence of catalytic amounts (about 3 grams) of 5% Pd/C at 10 atm of hydrogen for 5 hrs. The decolorized mixture was microfiltered (0.2-μm pore size) to yield a clear water-soluble soybean-based extract solution (2.3 liters).

The water-soluble soybean-based extract solution was characterized by high-pressure liquid chromatography (HPLC). The HPLC was conducted on a C18-reverse phase column 150 mm×4.6 mm, Symmetry Shield RP18 available from Waters, using a gradient elution method, 1 ml/min for 20 minutes with 15%–40% aqueous acetonitrile and 0.1% trifluoroacetic acid at 30° C. The HPLC detector was set at 254 nm. FIG. 1 shows the HPLC chart of the major components in the soluble soybean product in Example 1. Each of the peaks from the HPLC chart is listed in table 1 below along with their retention time, peak area, and percent area. Several individual components of the extract were identified by comparing the retention times of the unknown components to retention times of known isoflavone glycosides analyzed by HPLC under the same experimental conditions.

The water-soluble soybean-based extract solution was also characterized to determine the relative amounts of the components of the extract. A sample of the extract was sent to and analyzed by Food Products Laboratory Inc., located in Portland, Oreg., USA, using FDA approved methods. The extract included <0.1% fat, 5% protein, 65% carbohydrates (polysaccharides), 20% isoflavones, 8% minerals, and 1% moisture.

TABLE 1

HPLC analysis of soluble soybean product in Example 1

| Peak # | Retention Time (min) | Peak Area (mAU * sec) | Area (%) | Compound |
|---|---|---|---|---|
| 1 | 6.940 | 56.95 | 0.35 | N.D. |
| 2 | 7.231 | 85.42 | 0.53 | N.D. |
| 3 | 7.661 | 164.09 | 1.02 | N.D. |
| 4 | 8.090 | 5129.91 | 31.85 | Daidzin |
| 5 | 8.507 | 2722.58 | 16.90 | Glycitin |
| 6 | 10.376 | 19.68 | 0.12 | N.D. |
| 7 | 10.652 | 23.89 | 0.15 | N.D. |
| 8 | 11.069 | 34.82 | 0.22 | N.D. |
| 9 | 11.685 | 367.98 | 2.28 | N.D. |
| 10 | 11.990 | 1378.49 | 8.56 | Genistin |
| 11 | 12.766 | 75.19 | 0.47 | Malonyl Daidzin |
| 12 | 13.048 | 52.95 | 0.33 | Malonyl Glycitin |
| 13 | 13.461 | 3038.54 | 18.86 | Acetyl Daidzin |
| 14 | 13.771 | 1421.88 | 8.83 | Acetyl Genistin |
| 15 | 15.723 | 33.08 | 0.21 | N.D. |
| 16 | 15.942 | 43.63 | 0.27 | N.D. |
| 17 | 17.265 | 58.45 | 0.36 | N.D. |
| 18 | 17.737 | 867.85 | 5.39 | Acetyl Glycitin |
| 19 | 18.236 | 288.12 | 1.79 | Glycitein |
| 20 | 18.822 | 196.99 | 1.22 | Daidzein |
| 21 | 25.657 | 47.89 | 0.30 | Genistein |
| | Total | 16108.41 | 100.00 | |

N.D.: Not Determined

EXAMPLE 2

Pulverized soybean crude product (1 kg) extracted with about 90% aqueous EtOH, i.e., SoyLife 150 purchased from Schouten USA, Inc., was added to 27 liters of hot water. The mixture was stirred at 90° C. for 15 min. and then an aqueous solution (3 liters) of citric acid (90 g) was added to the mixture. The mixture was stirred at 90° C. for 15 min. The residue and solution were filtered through a Celite bed on paper filter under vacuum. The filtrate was a pale yellow clear solution (27 liters). Potassium carbonate (50 g) was added to the filtrate to adjust pH to 6.0. The filtrate was purified to remove bacteria by further filtering the filtrate with a 0.45 μM pore size filter (Millipore Corporation) under vacuum. The purified filtrate was then concentrated by using 2 inches wiped-film stills (Pope Scientific Inc.) at 70° C. under 20 mmTorr to yield a light yellow water-soluble soybean-based extract solution (18 liters).

EXAMPLE 3

A clear water-soluble soybean-based extract (2 liters) was obtained in the same manner as described in Example 1. The extract solution was then lyophilized using a lyophilizer manufactured by Bertis Corp for 2 days at −85° C. under 10 mm Torr, resulting in 350 g of a pale yellow dry cake. The cake, which contained 70 g of isoflavone derivatives, had a solubility of approximately 200 mg/ml. The solubility was tested by first adding 1 g of the dried extract into 1 ml of pure water at 25° C. with agitation for 5 min. If the extract was not completely dissolved (visual inspection), another 1 ml of water was added and the resulting mixture agitated for 5 minutes at 25° C. Next, the mixture was visually inspected to determine if the extract had completely dissolved. If not, water at 25° C. was added in 1 ml increments and agitated for 5 minutes after each addition of water until the extract was completely dissolved by visual inspection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A water-soluble bean-based extract prepared by a method comprising:

stirring a pulverized crude bean extract and a coagulant in heated water to form a suspension; and collecting a supernatant of the suspension to obtain a water-soluble bean-based extract; wherein the heated water has a temperature of 30–100° C.; and the water-soluble bean-based extract containing one or more isoflavone derivatives of the formula:

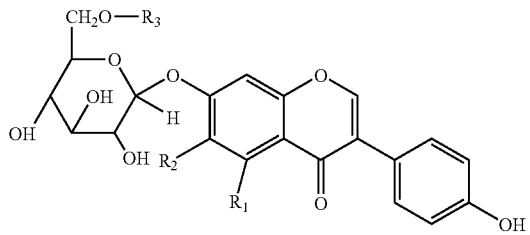

in which $R_1$ is hydrogen or hydroxy, $R_2$ is hydrogen or methoxy, $R_3$ is hydrogen or CO-$R_4$, $R_4$ being methyl or carboxymethyl; and the water-soluble bean-based extract, in dried form, includes from about 5 to about 50 parts by weight of isoflavone derivatives and has a solubility from 10 mg/ml to 1,000 mg/ml in water at about 25° C.

2. The water-soluble bean-based extract of claim 1, wherein the crude bean extract is prepared from soybeans, mung beans, black beans, or kidney beans.

3. The water-soluble bean-based extract of claim 2, wherein the crude bean extract is prepared from soybeans.

4. The water-soluble bean-based extract of claim 3, wherein the coagulant is an acid.

5. The water-soluble bean-based extract of claim 4, wherein the coagulant is an organic acid.

6. The water-soluble bean-based extract of claim 5, wherein the coagulant is citric acid, fumaric acid, lactic acid, malic acid, or tartaric acid.

7. The water-soluble bean-based extract of claim 6, wherein the coagulant is citric acid.

8. The water-soluble bean-based extract of claim 4, wherein the coagulant is an inorganic acid.

9. The water-soluble bean-based extract of claim 8, wherein the coagulant is HCl, $H_2S_4$, or $H_3P_4$.

10. The water-soluble bean-based extract of claim 1, wherein the coagulant is an acid.

11. The water-soluble bean-based extract of claim 10, wherein the coagulant is an organic acid.

12. The water-soluble bean-based extract of claim 11, wherein the coagulant is citric acid.

* * * * *